United States Patent
Nesterenko et al.

(10) Patent No.: US 11,801,117 B2
(45) Date of Patent: Oct. 31, 2023

(54) SYSTEMS AND METHODS FOR ENFORCING CLEANING OF A MEDICAL DEVICE

(71) Applicant: CareFusion 303, Inc., San Diego, CA (US)

(72) Inventors: Igor Nesterenko, San Diego, CA (US); Evan Chen, San Diego, CA (US); Lisa Diggett, Olathe, KS (US); Robert Regedanz, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 421 days.

(21) Appl. No.: 17/002,695

(22) Filed: Aug. 25, 2020

(65) Prior Publication Data
US 2021/0059784 A1   Mar. 4, 2021

Related U.S. Application Data

(60) Provisional application No. 62/891,890, filed on Aug. 26, 2019.

(51) Int. Cl.
*A61B 90/70* (2016.01)
*G05B 19/406* (2006.01)
(Continued)

(52) U.S. Cl.
CPC ........... *A61B 90/70* (2016.02); *G05B 19/406* (2013.01); *G05B 19/4155* (2013.01);
(Continued)

(58) Field of Classification Search
CPC .. A61B 90/70; A61B 2209/10; G05B 19/406; G16H 40/40
See application file for complete search history.

(56) References Cited

U.S. PATENT DOCUMENTS

| 2012/0092135 A1 | 4/2012 | Collins, Jr. et al. |
| 2012/0173274 A1* | 7/2012 | Rensvold ............. G08B 21/245 705/2 |

(Continued)

OTHER PUBLICATIONS

International Search Report and Written Opinion for Application No. PCT/US2020/047838, dated Nov. 2, 2020, 17 pages.
(Continued)

*Primary Examiner* — Vincent H Tran
(74) *Attorney, Agent, or Firm* — Morgan, Lewis & Bockius LLP

(57) ABSTRACT

Systems and methods for enforcing a cleaning of a medical device are disclosed. A method includes receiving an indication that a medical device has been exposed to a contaminate, providing, responsive to receiving the indication, an instruction to disable the medical device, receiving, after transmitting the instruction, cleaning information indicating that a cleaning of the medical device was attempted, identifying a predetermined cleaning procedure corresponding to the medical device and the contaminate, determining, based on the cleaning information, that the medical device was cleaned according to the predetermined cleaning procedure corresponding to the medical device and the contaminate, and enabling the medical device responsive to determining that the medical device was cleaned according to the predetermined cleaning procedure.

18 Claims, 7 Drawing Sheets

(51) Int. Cl.
  *G05B 19/4155* (2006.01)
  *A61M 5/142* (2006.01)
  *G06F 3/041* (2006.01)

(52) U.S. Cl.
  CPC ......... *A61M 5/142* (2013.01); *A61M 2209/10* (2013.01); *G05B 2219/35111* (2013.01); *G06F 3/041* (2013.01)

(56) References Cited

U.S. PATENT DOCUMENTS

| | | | | |
|---|---|---|---|---|
| 2014/0032232 | A1* | 1/2014 | Brown | G06Q 30/018 705/2 |
| 2017/0270258 | A1* | 9/2017 | Duckert | G16H 40/40 |
| 2018/0357385 | A1* | 12/2018 | LaPorte | A61L 2/08 |
| 2018/0360558 | A1* | 12/2018 | Bassion, Sr. | A61B 90/98 |
| 2019/0197268 | A1* | 6/2019 | Moreno | G06K 7/10366 |
| 2020/0289771 | A1* | 9/2020 | Russell | G05B 15/02 |
| 2021/0050099 | A1* | 2/2021 | Kirshenbaum | G16H 40/60 |
| 2021/0386508 | A1* | 12/2021 | Jackson | G01N 21/94 |

OTHER PUBLICATIONS

Remote Administration—Wikipedia (XP055801712), dated Jan. 18, 2013, last edited on May 3, 2021, Retrieved from https://en.wikipedia.org/w/index.php?title=Remote_administration&oldid=533679866, 5 pages.

Written Opinion from the International Preliminary Examining Authority for Application No. PCT/US2020/047838, dated Aug. 30, 2021, 13 pages.

International Preliminary Report on Patentability from the International Preliminary Examining Authority for Application No. PCT/US2020/047838, dated Dec. 14, 2021, 22 pages.

* cited by examiner

SYSTEMS AND METHODS FOR ENFORCING CLEANING OF A MEDICAL DEVICE

CROSS REFERENCE TO RELATED APPLICATIONS

This application claims the benefit of priority as a non-provisional application of U.S. Application Ser. No. 62/891,890, entitled "SYSTEMS AND METHODS FOR ENFORCING CLEANING OF A MEDICAL DEVICE," filed on Aug. 26, 2019, the entirety of which is incorporated herein by reference.

TECHNICAL FIELD

This application relates generally to enforcing cleaning of medical devices in healthcare organizations.

BACKGROUND

Medical devices used while treating a patient may be contaminated by an allergen, a disease, and/or an infection affecting the patient and/or a clinician treating the patient. Contamination of the medical devices may increase risk the spread of contamination to other clinicians, patients, and/or medical devices in the healthcare facility. Therefore, failure of successfully cleaning a contaminated medical device increases health risk of patients and employees of the healthcare facility.

SUMMARY

One concern for a healthcare organization includes ensuring the medical devices used in a healthcare organization are properly cleaned (e.g., disinfected, sterilized, etc.) for a subsequent use. However, existing devices are not known to detect whether they have been exposed or properly cleaned. Moreover, existing systems cannot identify all medical devices that have interacted with sick or contaminated individuals, and cannot track and identify whether every medical device associated with a patient or interacted with by a clinician treating the patient has been cleaned. Accordingly, the subject technology disclosed herein includes systems, devices, and methods that may be used to implement cleaning protocols, and enforce and verify that a medical device is properly cleaned before being used again.

The subject technology further provides systems and methods that can track and identify medical devices associated with a patient or that were interacted with by a clinician treating the patient, determining whether the medical devices are cleaned properly, and dynamically adjust one or more functions the medical devices until proper cleaning has been verified. Such systems and methods effectively reduce the risk of exposing medical devices, patients, and/or personnel of a healthcare facility to a contaminate.

In accordance with some implementations, a method includes determining, based on infection data associated with at least one of a patient or a clinician, a contaminated medical device. The method includes transmitting an instruction to the contaminated medical device to cause the contaminated medical device to disable. The method includes receiving identifying information of a cleaning solution from the contaminated medical device. The method includes determining, based on the identifying of the cleaning solution, whether the cleaning solution is correct. The method includes in response to determining that the cleaning solution is correct, causing one or more cleaning steps to be displayed on a display device associated with the contaminated medical device. Other aspects include corresponding systems, apparatus, and computer program products for implementation of the method.

In accordance with some implementations, a system includes a memory storing instructions and one or more processors coupled with the memory and configured to execute the instructions to cause the system to determine, based on infection data associated with at least one of a patient or a clinician, a contaminated medical device, transmit an instruction to the contaminated medical device to cause the contaminated medical device to disable, receive identifying information of a cleaning solution from the contaminated medical device, determine, based on the identifying of the cleaning solution, whether the cleaning solution is correct, and when the cleaning solution is correct, transmit one or more cleaning steps to be displayed on a display device associated with the contaminated medical device. Other aspects include corresponding systems, apparatus, and computer program products for implementation of the system In accordance with some implementations, a device management server includes one or more processors and memory storing one or more programs configured for execution by the one or more processors. The one or more programs include instructions for performing the operations of any of the methods described in this application. In accordance with some implementations, a non-transitory computer-readable storage medium stores instructions that, when executed by a server system, cause the server system to perform the operations of any of the methods described in this application.

BRIEF DESCRIPTION OF THE DRAWINGS

For a better understanding of the various described implementations, reference should be made to the Detailed Description below, in conjunction with the following drawings. Like reference numerals refer to corresponding parts throughout the figures and description.

Figure 1:
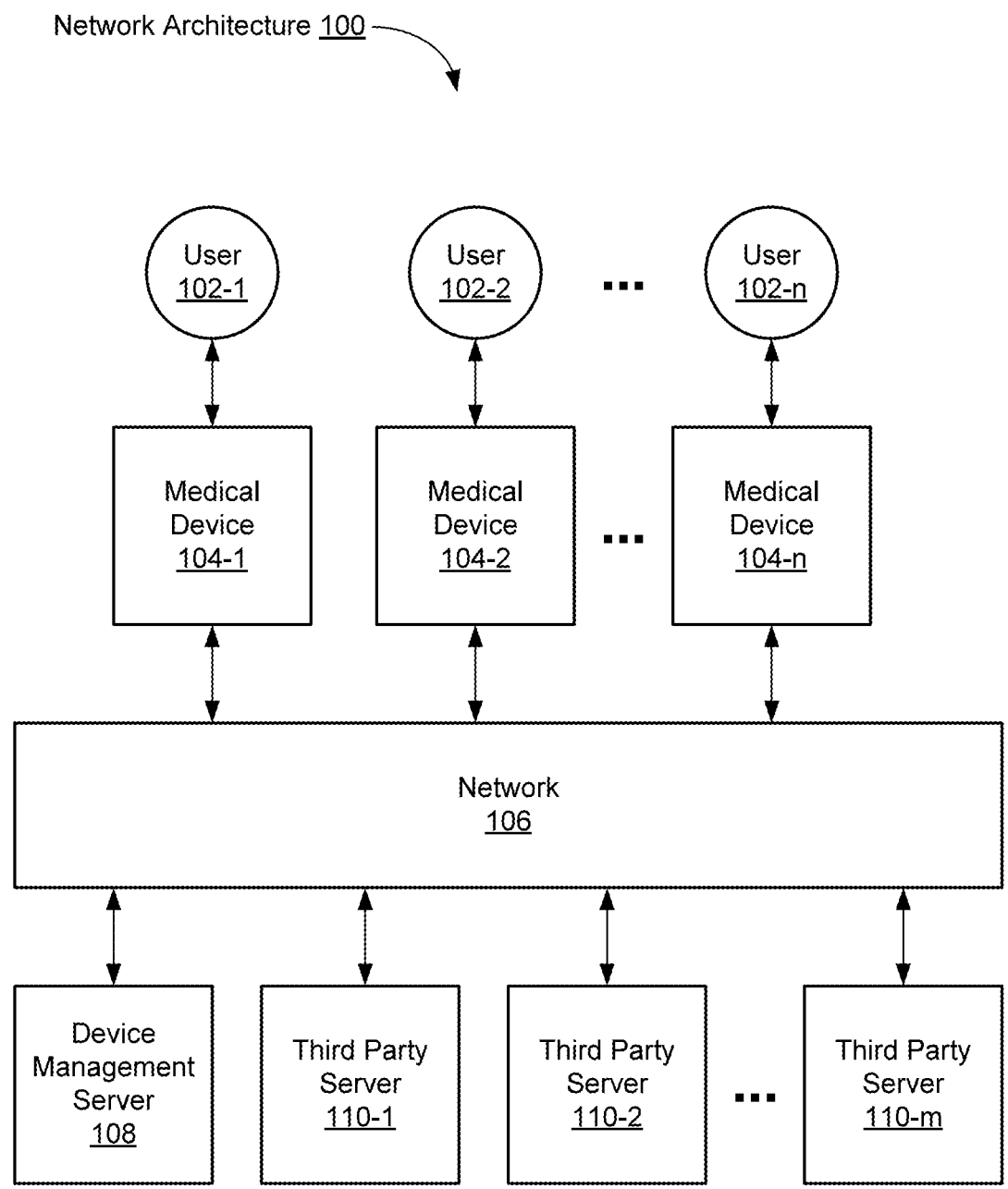
FIG. 1 is a block diagram of a network architecture for enforcing cleaning of one or more medical devices according to illustrative implementations.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various configurations of the subject disclosure and is not intended to represent the only configurations in which the subject disclosure may be practiced. The appended drawings are incorporated herein and constitute a part of the detailed description. The detailed description includes specific details for the purpose of providing a thorough understanding of the subject disclosure. However, it will be apparent to those skilled in the art that the subject disclosure may be practiced without these specific details. In some instances, structures and components are shown in block diagram form in order to avoid obscuring the concepts of the subject disclosure. Like components are labeled with identical element numbers for ease of understanding.

The subject technology identifies use of a medical device for a certain class of patients (e.g., an infectious patient) or care areas (e.g., an infectious environment). As will be described further, if a certain patient associated with the medical device is known to be contagious, or a clinician associated with the medical device is known to be sick, then the system may automatically adjust (e.g., lock, power down, and the like) the medical device so that a new patient or clinician cannot interact with the medical device until the impacted medical device is cleaned. In this regard, the medical device is taken out of service. In some implementations, all devices that an infected patient or clinician has touched are disabled (e.g., electronically locked). The system may then notify staff in all known locations where the device was located, touched, or programmed that the device is contaminated and has been taken out of service.

According to various implementations, the disclosed system is configured to track a medical device as it is used throughout a healthcare facility, including the locations in which the device is used and for which patients. The system may store a record for each device and, as clinicians interact with the device, the record may be updated to record the interaction. Each interaction with a patient may also be recorded. For example, when a clinician badges in to a medical device (e.g., logs in to a pump by swiping or moving an RFID tagged badge storing his or her credentials), the medical device may add the clinician to the record, and prompt the clinician to enter relevant information regarding the patient to add to the record. The hospital data system may include admission information, and other identifying information regarding the patient and/or the patient's current location in the healthcare organization. This information may be cross-indexed using the clinician or patient's identification, and added to the record associated with the device.

Patient information such as from an electronic medical record may include healthcare conditions of the patient, and/or potential contaminants carried by the patient. When a patient is associated with a medical device (e.g., by a clinician entering or scanning a patient identifier), the system may access the medical record, identify potential contaminants associated with the patient, and update the device record. In some implementations, the contaminants may be inferred by identifying other patients who may have been in proximity to the device, for example, by being in the same room with the patient assigned to the device and/or with medications administered or dispensed by the medical device. In such implementations, the identity of the patient or patient specific medical records may not be added to the record, or used to determine a cleaning status for the medical device. As used herein, a "contaminant" may include an undesirable biological (e.g., viruses, bacteria, or other cellular matter) or non-biological substance (e.g., chemical compounds, hazardous substance, or other particulates), and which may be at or suspected to be at a specified location, or affecting a patient associated with the medical device and/or a clinician that interacted with the medical device, or to which the medical device was exposed.

According to various implementations, when a clinician is identified as being exposed to a contaminant, all devices used the exposed clinician may be disabled (e.g., electronically locked). For example, the system may a measure time period from exposure to the infected patient, proximity to the infected patient, number of interactions with the patient within a period of time, and determine whether the medical device is infected based on a comparison of the measured value(s) against one or more thresholds. The clinician's contamination status may be assessed based on one or more of: specific patient interactions as recorded in an electronic medical records system (or other health information system), medications administered by the clinician, the clinician's assigned care area, or other information stored within the system. The system (e.g., a server) may send a signal to all affected devices, indicating that they are to be cleaned and instructing them to limit operations until such cleaning is verified.

Some medical devices include functional modules. The disclosed system may identify and disable medical devices based on an exposed functional module. For example, the medical device may include an infusion module used by an infected patient or clinician. Each module may include electromagnetic connectors with identifiers. The system may disable (e.g., electronically lock) or otherwise adjust the medical device and/or the functional module when the module is plugged in (e.g., to the medical device) and the system cannot verify that the module was cleaned since exposure.

According to various aspects, the disclosed system may enforce cleaning of a device or module until it is recommissioned. To satisfy cleaning requirements, the system may require certain information regarding a cleaning of the device be received before restoring full operation of the device. For example, the system may require that the medical device or functional module be identified (e.g., by global positioning system (GPS) or wireless connection) as being in a specific location corresponding to a cleaning location, and that a technician responsible for cleaning devices be identified as being associated with the device at the cleaning location. A cleaning technician may have a radio-frequency identification (RFID) tag that interacts with the device (e.g., by tapping on or swiping an RFID transceiver located on the device). When the device has been disabled due to a contaminate, the device may report all log in requests, and transmit a login request from the technician (in addition to the login location) to the system. Cleaning solution may also have an RFID tag identifying the solution, and this may also be scanned by the technician, and reported to the system by the medical device.

Each medical device and/or contaminate may require a specific cleaning procedure (e.g., solvent(s), time, area(s) of the device to be cleaned, verification requirements (e.g., witnessing, scanning, culture testing, etc.), and the like) to be performed before the device is enabled (e.g., electronically unlocked). The cleaning procedure may be dictated based on the medical device, potential patient or clinician contaminants, or other detectable characteristic of the medical device, patient treated with the medical device, or clinician using the medical device. The medical device may be programmed to require the cleaning technician to enter and verify which cleaning procedure was performed. Once the system verifies that the cleaning procedure was performed, the medical device and/or functional module may be electronically re-enabled for use. This may include electronically unlocking the device. Accordingly, the foregoing automatic enforcement improves cleaning practice and reduces the spread of infection throughout a healthcare organization.

The terminology used in the description of the various implementations described herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed terms. It will also be understood that, although the terms "first" and "second" are used herein to describe various elements, these elements should not be limited by these terms. These terms are used only to distinguish one element from another. It will be further understood that the terms "includes," "including," "comprises," and/or "comprising" when used in the specification, specify the presence of stated features, steps, operations, elements, and/or components, but do not preclude the presence or addition of one or more other features, steps, operations, elements, components, and/or groups thereof. A clinician may include a licensed or unlicensed individual responsible for operating, maintaining, servicing, delivering, or otherwise interacting with a medical device in, by, or for a healthcare organization. As used herein, examples of a healthcare organization include hospitals, long-term care facilities, nursing homes, out-patient treatment centers, store-front retail treatment centers, pharmacies, community clinics, non-acute care facilities, acute care facilities, and the like.

FIG. 1 is a block diagram of a network architecture 100 in accordance with some embodiments. In the depicted example, the network architecture 100 includes one or more medical devices 104-1, 104-2, . . . , 104-*n*, collectively referred to herein as medical devices 104. The one or more medical devices 104 may be communicatively coupled to a device management server 108 and/or one or more third-party servers 110-1, 110-2, . . . , 110-*m*, collectively referred to herein as third-party servers 110, by one or more communication networks 106. Examples of the one or more communication networks include, but are not limited to, an intranet, the Internet, cellular telephone networks, mobile data networks, wide area networks, local area networks, metropolitan area networks, and the like. In some implementations, the one or more communication networks 106 include a public communication network (e.g., the Internet and/or a cellular data network), a private communications network (e.g., a private LAN or leased lines), or a combination of such communication networks. The device management server 108 may be configured to communicate with the medical devices 104 and/or the third-party servers 110.

The device management server 108 may be configured to receive and/or transfer clinician related data from and/or to the medical devices 104 or the third-party servers 110. Examples of clinician related data include, but are not limited to, clinician identifiers, clinician biographical information, and/or the like.

In some implementations, the device management server 108 may be a single computing device such as a computer server, while in other implementations, the device management server 108 is implemented by multiple computing devices working together to perform the actions of a server system (e.g., cloud computing). According to various implementations, a device management server 108 may include, or be connected to, a hospital information server, and may include or have access to patient medical records and/or other information that may facilitate the tracking/tracing of contaminated medical devices, as disclosed herein. Additional details of the device management server 108 are described herein and with reference to FIG. 2. In some implementations, the healthcare server system 108.

The medical devices 104 may include one or more input devices (shown in FIG. 3) configured to receive inputs to the medical devices 104. The clinicians, such as users 102-1, 102-2, . . . , 102-*n*, collectively referred to herein as users 102, may interact with the one or more medical devices 104 via the one or more input devices. The users 102 may utilize the medical devices 104 to access the device management server 108 and/or third-party servers 110 to participate in corresponding services provided by the device management server 108 and/or third-party servers 110. For example, a medical device 104 may include a network interface operably connected to device management server 108, and a user interface for receiving user interactions for communicating with the server.

Figure 2:
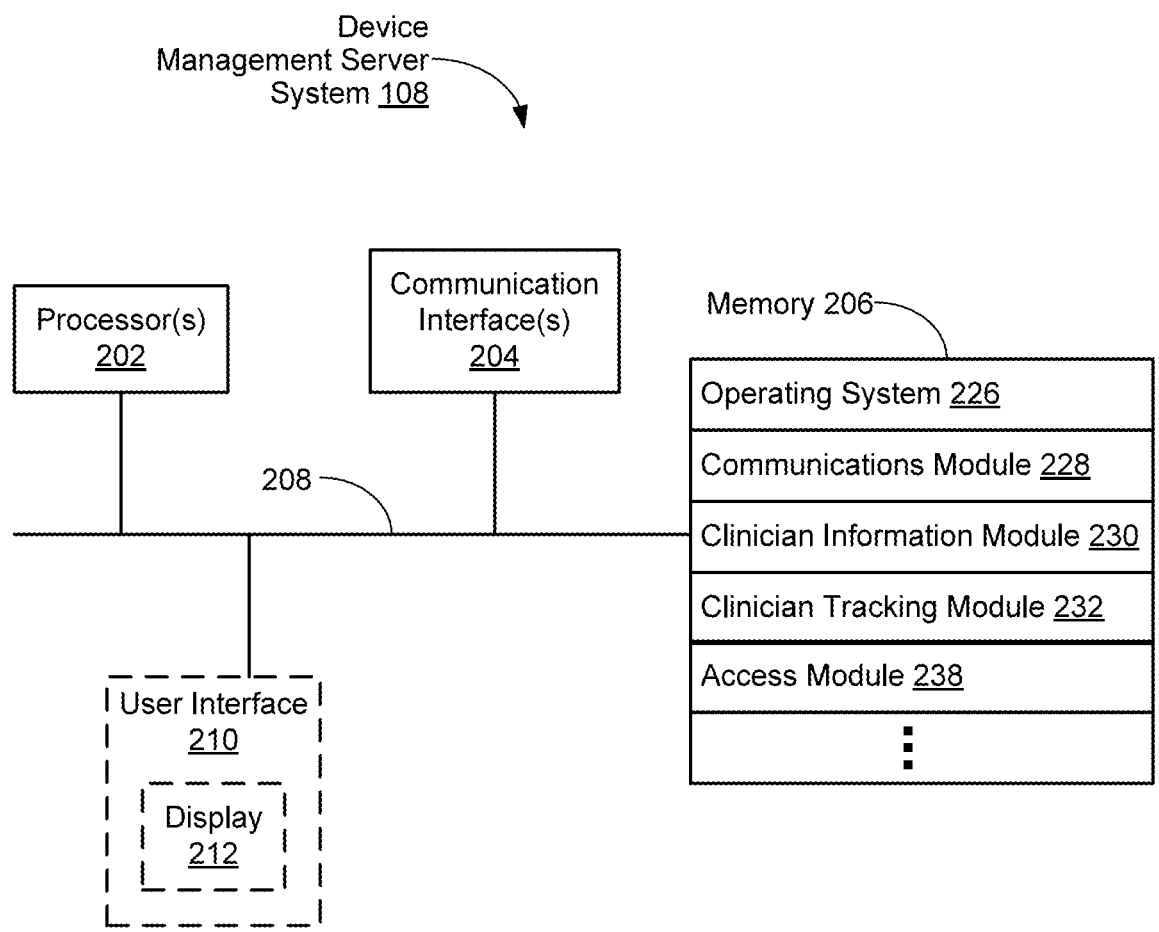
FIG. 2 is a block diagram of an exemplary server system from the architecture of FIG. 1 according to illustrative implementations.

Turning now to FIG. 2, there is shown a block diagram depicting a device management server 108 in accordance with some implementations. The device management server 108 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. In some implementations, the device management server 108 may include a display device 212. In some implementations, the device management server 108 may include input devices such as a keyboard, a mouse, a trackpad, and/or input buttons. In some implementations, the display device 212 may include a touch-sensitive surface, in which case the display is a touch-sensitive display.

The memory 206 may be a high-speed random-access memory, such as DRAM, SRAM, DDR RAM, or other random-access solid-state memory devices, and may include non-volatile memory, such as one or more magnetic disk storage devices, optical disk storage devices, flash memory devices, and/or other non-volatile solid-state storage devices. In some implementations, the memory 206 includes one or more storage devices remotely located from the processor(s) 202. The memory 206, or alternatively the non-volatile memory device(s) within the memory 206, includes a non-transitory computer-readable storage medium. In some implementations, the memory 206 or the computer-readable storage medium of the memory 206 stores programs, modules, and/or data structures that may be used for the performing one or more operations of the server system 108. For example, the memory 206 may include programs, modules, and/or data structures for an operating system 226, a network communication module 228, a clinician information module 230, a clinician tracking module 232, an access device module 238.

In some implementations, the operating system 226 module may include procedures for handling various basic system services and for performing hardware dependent tasks. The network communication module 228 may be configured for connecting the server system 108 to other computing devices via the one or more communication network interfaces 204 (wired or wireless) and one or more communication networks 106. The clinician information module 230 may be configured to store data related to clinicians including, but not limited to, clinician identifiers, clinician biographical information, care and the like. The clinician tracking module 232 may be configured to track information related to interactions of clinicians with the medical devices 104. In this regard, a medical device 104 may be connected to communication interface 204 over a network, and report interactions performed at the medical device to the tracking module 232 via the communication interface 204. The clinician tracking module 232 may track care areas visited by a clinician. The clinician tracking module 232 may be configured track interactions of clinicians over a predetermined period of time (e.g., a number of days). Additional details of the identifying contaminated medical devices and determining cleaning of medical devices are described herein with reference to FIGS. 5 and 6. The access module 238 may be configured to grant, deny, and/or modify access to the server system 108 and/or one or other computing systems or devices communicatively coupled to the server system 108. The access may be granted based on an identifier received for a clinician and comparing access permissions of the clinician with an access control list. The access control list may identify specific devices, modules, servers, or functions there of accessible by a clinician with an associated access permission (e.g., role or identifier).

Figure 3:
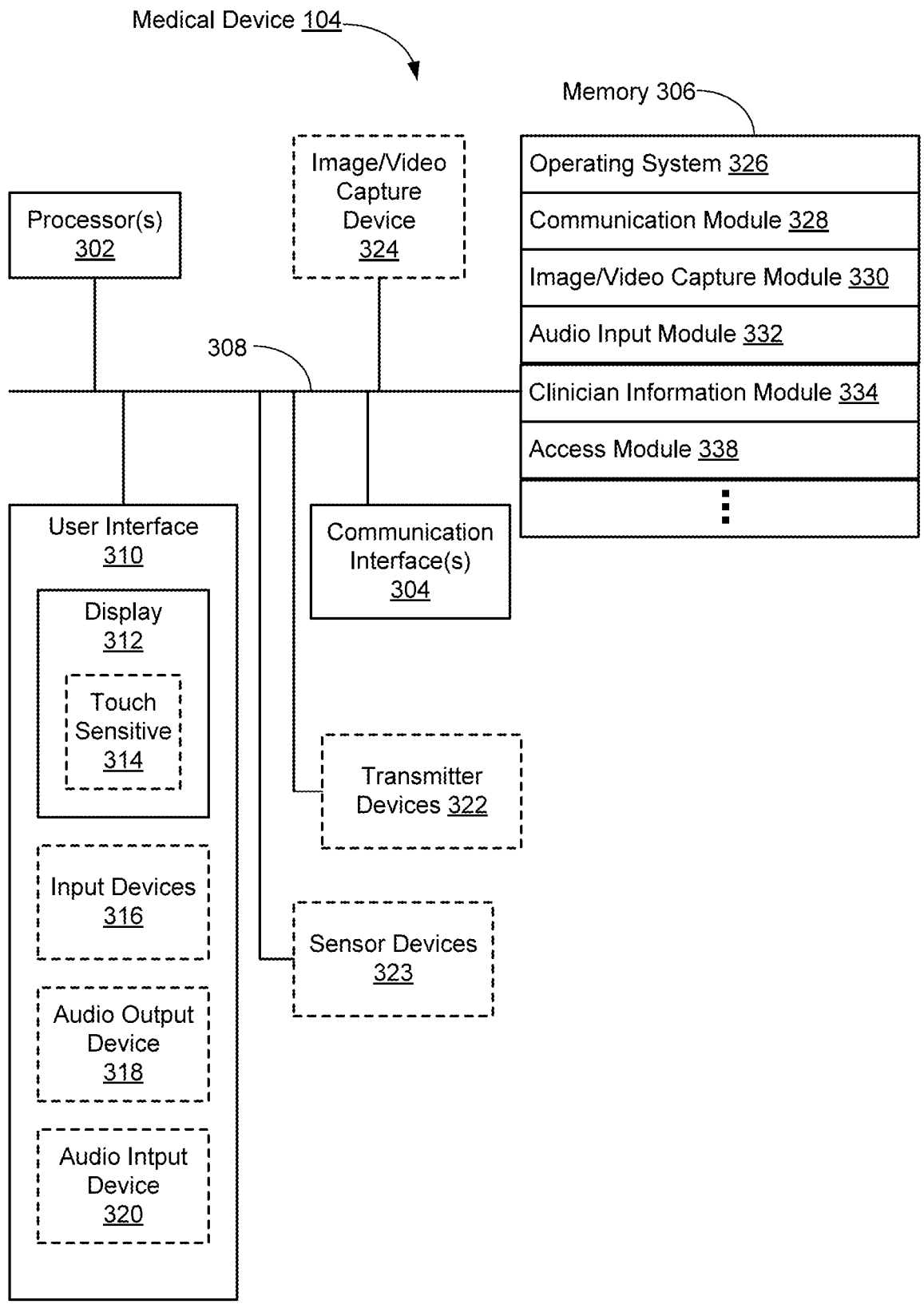
FIG. 3 is a block diagram of an exemplary client device from the architecture of FIG. 1 according to illustrative implementations.

Turning now to FIG. 3, there is shown a block diagram depicting a medical device 104. A medical device 104 may include one or more processors 302, one or more network or communications interfaces 304, memory 306, one or more communication buses 308, a user interface unit 310, transmitter devices 322, and sensor devices 323. The one or more processors 302, the one or more network or communication interfaces 304, memory 306, and the user interface unit 310 may be configured to communicate with one another via the one or more communication buses 308. In some implementations, the communication buses 308 may include circuitry (sometimes called a chipset) that interconnects and controls communications between components of the medical device 104. In some implementations, the medical device 104 may include an image/video capture device 324, such as a camera.

The user interface unit 310 may include a display 312, one or more input devices 316, such as a keyboard or a mouse, one or more audio output devices 318, and/or one or more audio input devices 320. In some implementations, the display 312 may include a touch sensitive display or surface 314, which is configured to receive touch-based inputs from a user 102. For example, display 312 may implement a resistive or capacitive sensing mechanism, or other sensing mechanism. In some implementations, the display 312 sensing mechanism may be configured to sense degrees of pressure in a user's touch and respond differently based on the amount of pressure exerted. The one or more audio output devices 318 may include, but are not limited to, speakers, interfaces configured to transfer audio related data to a device configured to project audio, and the like. The one or more input devices 320 may include, but are not limited to, microphones, interfaces configured to receive audio related data from a device configured to receive audio.

The memory 306 includes high-speed random-access memory, such as DRAM, SRAM, DDR RAM or other random-access solid-state memory devices; and may include non-volatile memory, such as one or more magnetic disk storage devices, optical disk storage devices, flash memory devices, or other non-volatile solid-state storage devices. In some implementations, the memory 306 includes one or more storage devices remotely located from the processor(s) 302. The memory 306, or alternatively the non-volatile memory device(s) within the memory 306, includes a non-transitory computer-readable storage medium. In some implementations, the memory 306 or the computer-readable storage medium of the memory 306 stores the programs, modules, and data structures that may be used for performing operations of the medical device 104 and for performing techniques described herein for enforcing cleaning of the medical devices 104. The memory 306 may include an operating system 326, a network communication module 328, an image/video capture module 330, an audio input/output module 332, a clinician information module 334, and the like.

The operating system 326 may be configured to perform procedures of execution of various system services of the medical device 104, including, but not limited to, hardware, and software dependent tasks. The network communication module 328 may be configured to execute instructions to connect the medical device 104 to one or more other computing devices, such as the healthcare server system 108, third party servers 110, and the like, via the one or more communication interfaces 304 and communication networks, such as the communication network 106. The image/video capture module 330 may be configured to execute instructions to capture images or a continuous stream of images. The audio input module 332 may be configured process received input data and transmit instructions and/or related data to one or more other components of the medical device 104. The access module 338 may be configured grant, deny, and/or modify access to the medical device 104. For example, the access module 338 may be configured to grant or deny access to the medical device 104 based on received login credentials for the medical device 104.

The above identified modules and applications may correspond to a set of executable instructions for performing one or more functions of the subject technology, as described above and/or in the methods described in this application (e.g., the computer-implemented methods and other information processing methods described herein). One or more of the modules may be implemented as a specific hardware device with the appropriate input and output signal paths. The modules may be combined or otherwise re-arranged in various implementations. In some implementations, the memory 206 and/or the memory 306 store a subset of the modules and data structures identified above. In some implementations, the memory 206 and/or the memory 306 stores additional modules and data structures not described above.

Figure 4:
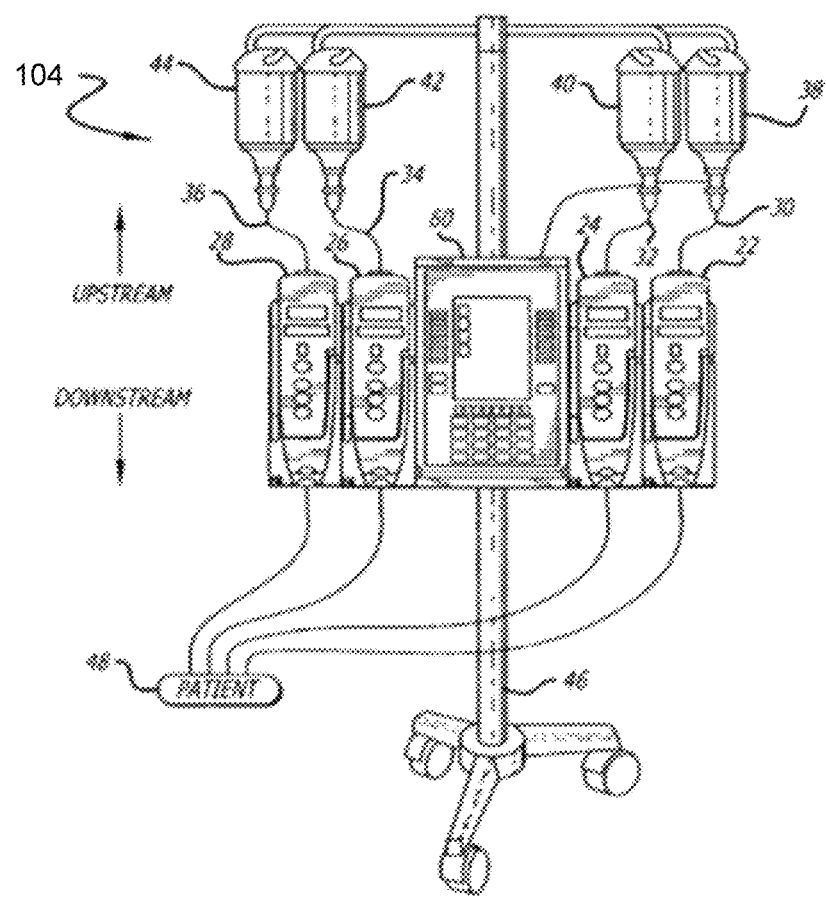
FIG. 4 is an example medical device which may be interacted with by a clinician within in a healthcare organization

FIG. 4 is an example medical device which may be interacted with by a clinician within in a healthcare organization. The medical device 104 shown in FIG. 4 may be configured to be connected to one or more functional modules, such as the four fluid infusion pumps 22, 24, 26, and 28 each of which is in operative engagement with a respective fluid administration set 30, 32, 34, and 36. Fluid supplies 38, 40, 42, and 44, which may take various forms but in this case are shown as bottles, are inverted and suspended above the pumps. Fluid supplies may also take the form of bags or other types of containers. Both the medical device 104 and the fluid supplies 38, 40, 42, and 44 are mounted to a roller stand or pole 46. The specific fluid supplies as well as their orientation (e.g., mount location, mount height, mounting type, etc.) within the care area may be generate one or more interaction records. The interaction record for a set for example may be generated in part by detecting a scannable code associated with the set prior to use. Once scanned, the interaction record may be recorded for use as described herein.

As shown in the example implementation of FIG. 4, each administration set 30, 32, 34, and 36 is connected between a respective fluid supply 38, 40, 42, and 44 and the same patient 48 so that the patient may receive the fluids in all the fluid supplies. The administration set may be identified either actively by, for example, scanning by a clinician or passively by, for example, wireless or optical detection of the administration set. As with the fluid supply, once identified, an interaction record may be generated identifying the administration set and one or more of the clinician, programming module, pump, administration set positioning (e.g., administration location (e.g., left forearm, right upperarm, etc.).

A separate infusion pump 22, 24, 26, and 28 may be used to infuse each of the fluids of the fluid supplies into the patient. The infusion pumps are flow control devices that will act on the respective tube or fluid conduit of the fluid administration set to move the fluid from the fluid supply through the conduit to the patient 48. Because individual pumps are used, each can be individually set to the pumping or operating parameters required for infusing the particular medical fluid from the respective fluid supply into the patient at the particular rate prescribed for that fluid by the clinician. The activities performed by the pump or clinician to infuse the particular medical fluid may be associated with one or interaction which may be recorded and processed as described.

Typically, medical fluid administration sets have more parts than are shown in FIG. 4. Many have check valves, drip chambers, valved ports, connectors, and other devices well known to those skilled in the art. These other devices have not been included in the drawings so as to preserve clarity of illustration.

Figure 5:
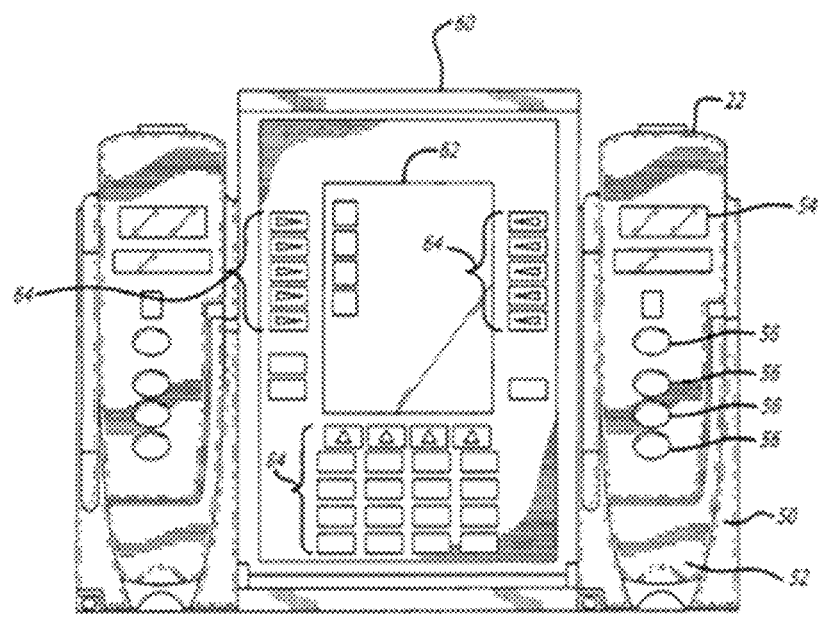
FIG. 5 is a closer view of a portion of the medical device shown in FIG. 4.

FIG. 5 is a closer view of a portion of the medical device shown in FIG. 4. FIG. 5 shows two of the fluid infusion pumps mounted at either side of a programming module, and the displays and control keys of each, with the programming module being capable of programming both infusion pumps. The pump 22 includes a door 50 and a handle 52 that operates to lock the door in a closed position for operation and to unlock and open the door for access to the internal pumping and sensing mechanisms and to load administration sets for the pump. When the door 50 is open, the tube can be connected with the pump 22. When the door 50 is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump 22, such as alert indications (e.g., alarm messages). Control keys 56 exist for programming and controlling operations of the infusion pump as desired. In some implementations, the control keys may be omitted and be presented as interactive elements on the display 54 (e.g., touchscreen display). The infusion pump 24 also includes audio alarm equipment in the form of a speaker (not shown).

In the embodiment shown in FIG. 4, a programming module 60 is attached to the left side of the infusion pump 24. Other devices or modules, including another infusion pump, may be attached to the right side of the infusion pump 24, as shown in FIG. 4. In such a system, each attached pump represents a pump channel of the overall medical device 20. In one embodiment, the programming module is used to provide an interface between the infusion pump 24 and external devices as well as to provide most of the operator interface for the infusion pump 24. Attention is directed to U.S. Pat. No. 5,713,856 entitled "Modular Patient Care System" to Eggers et al. incorporated herein by reference in which the programming module is described as an advanced interface unit.

Returning to FIG. 5, the programming module 60 includes a display 62 for visually communicating various information, such as the operating parameters of the pump 24 and alert indications and alarm messages. The programming module 60 may also include a speaker to provide audible alarms. The programming module 60 may also include one or more input devices, such as control keys 64 or a bar code scanner (not shown) for scanning information relating to the infusion, the patient, the clinician, or other. In some implementations, the display 62 may be implemented as a touchscreen display (e.g., display 312). In such implementations, the control keys 64 may be omitted or reduced in number by providing corresponding interactive elements via a graphical user interface presented via the display 62. The programming module 60 may include a communications system (not shown) with which the programming module 60 may communicate with external equipment such as a medical facility server or other computer and with a portable processor, such as a handheld communication device or a laptop-type of computer, or other information device that a clinician may have to transfer information as well as to download drug libraries to a programming module 60 or pump. The communication module may be used to transfer access and interaction information for clinicians encountering the programming module or device coupled therewith (e.g., pump 22 or bar code scanner). The communications system may include one or more of a radio frequency (RF) system, an optical system such as infrared, a BLUETOOTH™ system, or other wired or wireless system. The bar code scanner and communications system may alternatively be included integrally with the infusion pump 24, such as in cases where a programming module is not used, or in addition to one with the programming module 60. Further, information input devices need not be hard-wired to medical instruments, information may be transferred through a wireless connection as well.

The embodiment shown in FIG. 5 includes a second pump module 26 connected to the programming module 60. As shown in FIG. 4, more pump modules may be connected. Additionally, other types of modules may be connected to the pump modules or to the programming module such as syringe pump module, oximeter reader module, patient controlled analgesic module, or the like. Each module may generate interaction records of one or more interaction types. The interaction record may include an identifier of the module or device with which the interaction was conducted. The identifier may include a device type identifier, a model or series identifier, or a unique identifier for a specific device.

Figure 6:
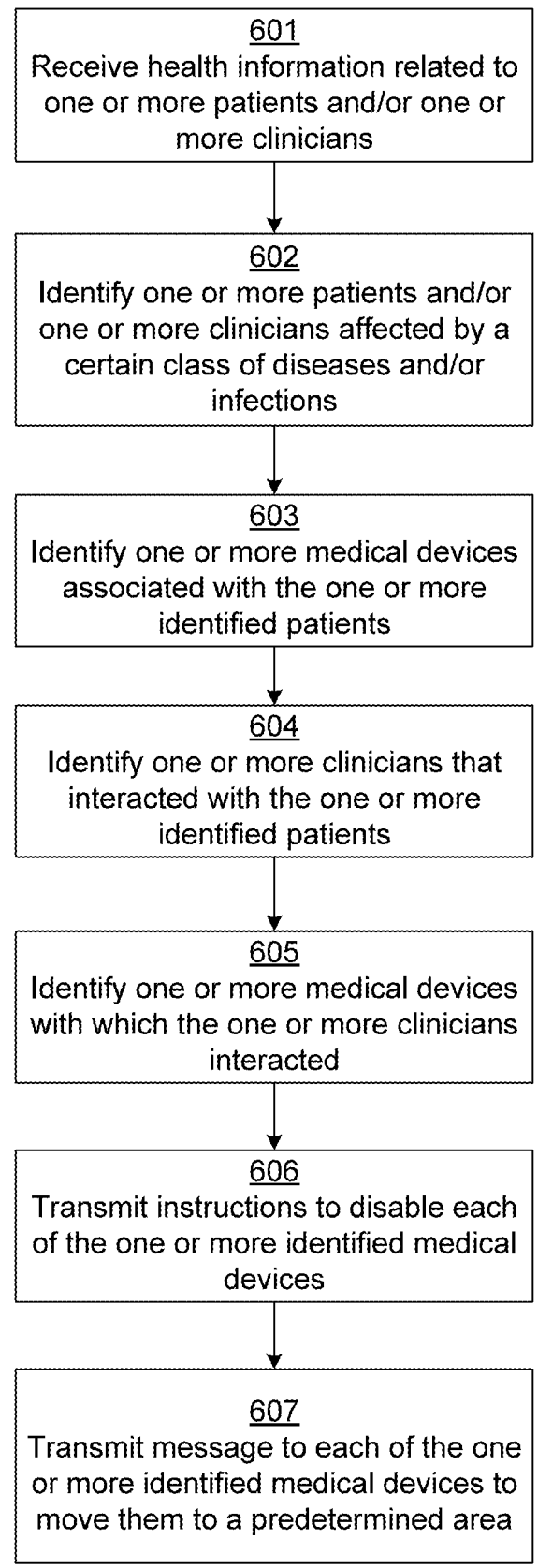
FIG. 6 is a flow chart of an example process of identifying one or more contaminated medical devices and enforcing cleaning of the contaminated medical devices according to illustrative implementations.

Turning now to FIG. 6, there is a shown a flowchart illustrating a process of identifying one or more contaminated medical devices and enforcing cleaning of the contaminated medical devices. For the purpose of illustrating a clear example, components of the network architecture 100, shown and described with reference to FIG. 1, components of the device management server 108, shown and described with reference to FIG. 2, and components of the medical devices 104, shown and described with reference to FIG. 3, may be used to describe the process of identifying one or more contaminated medical devices and enforcing cleaning of the contaminated medical devices.

The method 600 includes receiving, by the processor 202 of the device management server 108, health information related to one or more patients and/or treatments and/or one or more clinicians (block 601). The device management server 108 may receive health information related to one or more patient from a one or more patient information systems (e.g., from the patient's medical record, provided by an electronic medical record system). Similarly, the device management server 108 may receive health information related to one or more clinicians from a clinician or an employee information system. In some implementations, the processor 202 may store the received health information of each patient and/or or a clinician in association with a corresponding identifier of the patient and clinician. The received health information of each patient and/or clinician may indicate a contaminate (e.g., one or more allergens, diseases, and/or infections) affecting the patient and/or the clinician. For example, if a patient or a clinician is affected by Methicillin-resistant *Staphylococcus aureus* (MRSA), then one or more fields of the received health information and/or a combination thereof may indicate that the patient is affected by MRSA. As described further below, a clinician may be associated with a contaminate by virtue of having been associated with a patient having the allergen or disease or infection.

The processor 202 identifies one or more patients and/or clinicians affected by a certain class of allergens, diseases, and/or infections (block 602). The device management server 108 may be configured with a set of rules that categorize various allergens, diseases, and/or infections into various classes of allergens, diseases, and/or infections, and each class of allergen, disease, and/or infection may indicate a different level of health risk to a human being. In some implementations, the set of rules may categorize allergens, diseases, and/or infections into the different classes based at least on whether an allergen, a disease, and/or an infection is contagious. Based on the set of rules and the health information received at block 601, the processor 202 may be configured to identify the one or more patients and/or the clinicians affected by the certain class. In some implementations, the set of rules may specify a health risk score (e.g., a number ranging between 0 and 100) for each of the different classes of allergens, diseases, and/or infections, and the processor 202 may be configured to identify patients affected by a class of allergens, diseases, and/or infections that satisfies a threshold health risk score. For example, if the threshold health risk score is 80, then the processor 202 may be configured to identify one or more patients that are affected by a class of allergens, diseases, and/or infections with a health risk score above and/or equal to 80. The health risk score may be based on a number of interactions the clinician had with an infected patient (e.g., increasing with an increasing number of interactions). The health risk score may be based on the clinicians proximity to or distance from an infected patient (e.g., whether within a predetermined threshold distance).

The processor 202 identifies one or more medical devices associated with the one or more identified patients (block 603). The device management server 108 may receive a unique identifier of each medical device used for a patient, and the processor 202 may store the unique identifier of the medical device in association with an identifier of the patient in a data storage system associated with the device management server 108. In some implementations, the device management server 108 may receive data related to one or more medical devices used for a patient, including, but not limited to identifiers of the medical devices, may be received from one or more patient information systems and/or health information systems of a healthcare facility. The processor 202 may identify the one or more medical devices associated with the one or more identified patients based on the identifiers of those patients and the one or more devices stored in association with the patients. The identification at block 603 may limit the number of devices identified by restricting the time of use. For example, the contamination of devices during a visit one year ago may not be as relevant as for devices interacted with in the past seven days.

The processor 202 identifies one or more clinicians that interacted with the one or more identified patients (block 604). In some implementations, a clinician that interacts with the patient may log into a medical device associated with the patient and the device management server 108 may receive a unique identifier associated with that clinician from the login details of the clinician provided to the medical device associated with the patient. In this way, the device management server 108 may receive data related to one or more clinicians that interacted with a patient from a patient information system (e.g., electronic medical record system), and the processor 202 of the device management server 108 may store the received data related to the one or more clinicians in association with the patient. For example, the received clinician data may be stored in association with an identifier of the patient, in a data storage system associated with the device management server 108. In some implementations, for each of the one or more clinicians that interacted with the patient, the device management server 108 may receive a unique identifier of the clinician, and the processor 202 may store the unique identifier in association with an identifier of the patient in a data storage system associated with the device management server 108. Similar to block 603, time may be used to improve the efficiency and accuracy of the clinician interaction identification at block 604.

The processor 202 identifies one or more medical devices with which the one or more clinicians interacted (block 605). The one or more clinicians may be identified as clinicians that are affected by a certain class of allergens, diseases, and/or infections. For example, device management server 108 (and processor 202) may receive an indication that the clinician is treating a patient by way of the clinician logging into a medical device (e.g., an infusion pump) that is currently administering a medication to a patient, or that provides a medication for delivery to the patient (e.g., an automated dispensing device), or that is used to prepare medication for delivery to the patient (e.g., a medication preparation workstation). The clinician may log into the medical device by providing an identifier to the medical device to interact with the medical device (e.g., by swiping a badge and transmitting the identifier using RFID technology), and the device management server 108 may receive the identifier of the clinician from the medical device when the clinician provides the unique identifier to the medical device. For each medical device that a clinician interacts with, the processor 202 may store the unique identifier of the clinician in association with the identifier of the medical device in a data storage system associated with the device management server 108. The processor 202 may be configured to identify the one or more medical devices with which the one or more clinicians interacted based on the identifiers of the one or more clinicians and the associations between the identifiers of the one or more clinicians and the one or more medical devices.

On identifying a potential contamination of the one or more medical devices, processor 202 transmits instructions to disable (e.g., electronically lock) each of the one or more identified medical devices (block 606). The processor 202 may update a current status and/or a current state of the identified medical devices as disabled (e.g., "locked") in response to transmitting the instructions to the identified medical devices. The status or state may cause the device management server 108 to prevent clinicians from logging into the medical device unless certain criteria are met (e.g., clinician is a cleaning technician, the medical device is located in a predetermined cleaning area, etc.). The processor 202 transmits a message to each of the one or more identified medical devices to move them to a predetermined area (block 607). The device management server 108 causes the transmitted message to be displayed on a display device associated with an identified medical device (e.g., display device of the identified medical device). A medical device may be configured to display the received message from the device management server 108 on a display device associated with the medical device. Disabling the medical device may include activating a physical element of the medical device to prevent further use. For example, an actuator may cause a pin to engage the handle 52 to prevent opening of the door 50 of an affected pump. As another example, the fluid pump may include an occluding mechanism to prevent fluid from flow through a tube. The instructions may engage the occluding mechanism thereby obstructing the pumping pathway of the fluid pump and preventing a new tube from being loaded into the pump. As another example, the pumping module 60 may provide power or other resources to connected modules. The instructions to disable may include a control signal to disable power provided by the pumping module 60. The control signal may reduce the voltage provided or cause the power circuit with the connected modules to break until the appropriate cleaning is performed. In some implementations, the medical device or mounting element (e.g., pole) may include locomotive components such as wheels and a motor. In such implementations, the instruction may cause the medical device to navigate to the predetermined area.

In some implementations, the device management server 108 may be configured to receive location data of a medical device, and the processor 202 may determine whether the medical device is within the predetermined area based on the received location data of the medical device. The location of the medical device may be determined by way of a (global positioning system) GPS locator system within the medical device, or by identifying that the medical device is currently transmitting over or connecting with a particular WiFi transceiver at a known location.

A hospital organization may include multiple predetermined care areas, including intensive care units (ICU), operating rooms, emergency rooms, maternity wards, general patient wards, and the like. In some implementations, a medical device (or functional module) may be identified as being contaminated by way of being in an area identified as being a contaminated area. The area may be identified as being contaminated based on a patient residing in the area who has been infected with a predetermined contaminant or infection. The area may be identified based on identifying that the patient moved to or through the area, or by a threshold number of interactions of a caregiver in the area who also had a threshold number of interactions with the infected patient. In some implementations, device management server 108 may receive an indication that an area of the healthcare facility has been contaminated and issue an instruction (e.g., over a network) to disable (e.g., electronically lock) all medical devices (and/or functional modules) in the contaminated area.

In some implementations, the processor 202 may be configured to determine whether an identified medical device is moved to the predetermined area within a threshold amount of time since transmitting the message to move the medical device to the predetermined area, and/or since transmitting instructions to disable (e.g., electronically lock) the medical device. For example, once the device is flagged as being contaminated, processor (or device management server 108) may monitor the location of the device to ensure it is moved to a predetermined cleaning area. The cleaning are determined for cleaning of the device may be based on the type of contaminate. If the processor 202 determines that the identified medical device is not moved to the predetermined area within the threshold amount of time, then the processor 202 may transmit a message to users of the medical device (e.g., cleaning personnel) to move the identified medical device to the predetermined area. In some implementations, the processor 202 may transmit an instruction to the medical device to cause the medical device to generate an aural alarm and/or display a visual alert on a display device associated with the medical device indicating that the medical device has not been moved to the predetermined area within a threshold amount of time.

As described further below, the device management server 108 may be configured to transmit instructions to a medical device to unlock the medical device in response to determining that the medical device is sufficiently cleaned. Additional details of transmitting determining whether a medical device is sufficiently cleaned and transmitting instructions to the medical to unlock the medical device are described with reference to FIG. 7.

Figure 7:
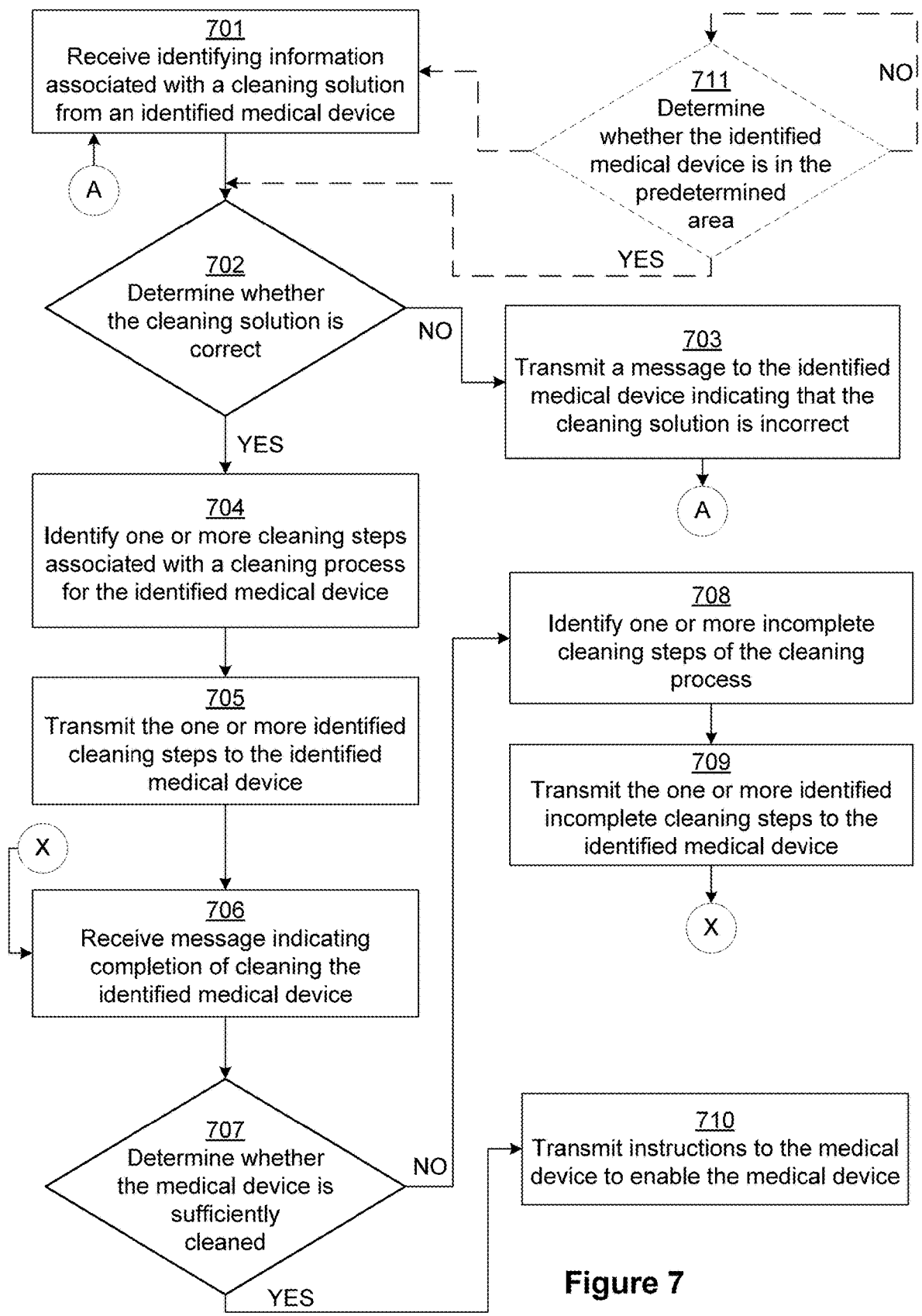
FIG. 7 is a flow chart of determining whether a medical device is sufficiently cleaned and transmitting instructions to enable the medical device according to illustrative implementations.

Turning now to FIG. 7, there is shown a flowchart illustrating an example process of determining whether a medical device is sufficiently cleaned and transmitting instructions to enable (e.g., electronically unlock) the medical device. For the purpose of illustrating one example, components of the network architecture 100, shown and described with reference to FIG. 1, components of the device management server 108, shown and described with reference to FIG. 2, and components of the medical devices 104, shown and described with reference to FIG. 3, may be used to describe the process of determining whether a medical device is sufficiently cleaned and transmitting instructions to unlock the medical device.

In the depicted example, a method 700 includes receiving, by the processor 202 of the device management server 108, identifying information associated with a cleaning solution being applied to an identified medical device (block 701). The identifying information may be received directly from a database (by an indexing based on the type of device), from the medical device or, in some implementations, via a device associated with a technician responsible for cleaning the medical device. In this regard, processor 202 (or system 108) may enforce a specific type of solution for a specific type of infection (e.g., blood spills, chemo spills, or normal dirt). When the device has been designated for cleaning, a technician may be prompted (e.g., by the medical device) to input the cleaning solution used to clean the medical device. The input may be by way of entering an identification of the cleaning solution via the input devices 316 or 320. In some implementations, the input may be by way of the medical device prompting the technician to place the cleaning solution proximate to the capture device 324 so that the cleaning solution may be optically identified by an optical sensor associated with the medical device. Optical identification may be, for example, by way of scanning a bar code on the cleaning solution container or by image recognition of the cleaning solution container. In some implementations, the identification may be by way of the technician selecting the cleaning solution from a plurality of cleaning solution options presented on a menu of the display of the medical device.

As described above, the identified medical device is placed in a disabled (e.g., electronically locked) state in response to receiving instructions to disable the medical device from the device management server 108. In some implementations, the processor 202 may determine whether the identified medical device is in a predetermined area of a healthcare facility associated with cleaning medical devices, in response to the device management server 108 receiving identifying information associated with a cleaning solution, as shown by block 711. As described above, the device management server 108 may receive location data of medical devices (e.g., from a GPS within the medical device or based on an input or scanning of the device received from the technician), and the processor 202 may determine whether a medical device is in the predetermined area based on the received location data. If the processor 202 determines that the medical device is not in the predetermined area, then the processor 202 may continue to periodically determine whether the medical device is in the predetermined area until the medical device is determined to be in the predetermined area. If the processor 202 determines that the medical device is in the predetermined area, then the method 700 may proceed to block 702.

The processor 202 determines whether the cleaning solution is correct (block 702). In some implementations, a medical device may be associated with one or more cleaning solutions, where the associated one or more cleaning solutions may be predetermined to be suitable and/or appropriate for the medical device based on the type of medical device and/or the type of allergen, disease, and/or infection currently associated with the medical device. For example, a medical device comprising a display device may be associated with a predetermined cleaning solution configured to clean a display device without damaging the display device. Similarly, a medical device may comprise a pumping module and/or include a pump, and the medical device may be associated with a cleaning solution configured to clean pump components. In some implementations, a set of rules may specify one or more cleaning solutions for different allergens, diseases, and/or infections, and/or for different classes of allergens, diseases, and/or infections. For example, a set of rules may specify one or more cleaning solutions for MRSA, and the set of rules may specify one or more different cleaning solutions for a different allergen, disease, and/or infection. The processor 202 may be configured to determine whether the cleaning solution is correct based on one or more cleaning solutions associated with the identified medical device. In some implementations, the processor 202 may determine whether the cleaning solution is correct based on whether the cleaning solution is suitable for the allergen, disease, and/or infection of the patient associated with the medical device and/or the clinician that interacted with the medical device.

If the processor 202 determines that the cleaning solution is not correct ('NO' at block 702), then the method 700 proceeds to block 703. The processor 202 transmits a message to the identified medical device indicating that the cleaning solution is incorrect (block 703). In some implementations, the processor 202 identifies one or more correct cleaning solutions based on one or more cleaning solutions associated with the identified medical device and/or the allergen, disease, and/or infection of the patient associated with the identified medical device and/or the clinician that interacted with the medical device. In some implementations, the processor 202 may identify one or more correct cleaning solutions based on a set of rules that specify one or more cleaning solutions for different medical devices, and/or different allergens, diseases, and/or infections, and/or different classes of allergens, diseases, and/or infections. The set of rules may be stored in a data storage system associated with the device management server 108.

If the processor 202 determines that the cleaning solution is correct ('YES' at block 702), then the method 700 proceeds to block 704. The processor 202 identifies one or more cleaning steps associated with the cleaning process for the identified medical device (block 704). According to various implementations, device management server system 108 may include a data repository storing predetermined cleaning procedures required for cleaning medical devices. Each type of medical device and each type of contaminant (e.g., infection, disease, and/or allergen) may be associated with one or more stored cleaning procedures. In this regard, once a medical device is identified for cleaning (and, e.g., electronically locked), the correct cleaning procedure may be identified based on the type of medical device or serial number, and/or based on the contaminant associated with the medical device, as discussed above.

A medical device may be associated with one or more cleaning processes based on one or more components (e.g., display device) of the medical device and/or one or more functional modules (e.g., a pump module) of the medical device. For example, a medical device comprising a display device may be associated with a cleaning process that include one or more cleaning steps for cleaning the display device of the medical device. Similarly, a medical device comprising and/or connected to a pump module may be associated with a cleaning process that includes one or more cleaning steps for cleaning the pump module. In some implementations, the processor 202 may be configured to identify a cleaning process for a medical device based on one or more functional modules connected to the medical device. For example, if a medical device is connected to a large volume pump module and a syringe module, then the processor 202 may identify one or more cleaning processes associated with cleaning a large volume pump module and the syringe module. In some implementations, contaminants such as an allergen, a disease, and/or an infection, and/or a class of allergens, diseases, and/or infections may be associated with one or more cleaning steps, and the processor 202 may identify one or more cleaning steps based on contaminants such as an allergen, a disease, and/or an infection affecting the patient associated with the medical device and/or a clinician that interacted with the medical device. The contaminant may also include a hazardous substance processed or stored by the medical device.

The processor 202 transmits the one or more identified cleaning steps to the identified medical device (block 705).

The processor 202 may cause the identified medical device to display the one or more identified cleaning steps on a display device associated with the identified medical device by transmitting the one or more cleaning steps to the identified medical device. As described above, in some implementations, the medical device 104 may comprise one or more modules, and the processor 202 may transmit the one or more identified cleaning steps to at least one of the one or more modules to cause the identified cleaning steps to be displayed on a display device of the at least one module. For example, a medical device 104 may comprise a core patient care unit (PCU) module, such as a programming module 60 shown in FIG. 4, and the processor 202 may transmit the one or more identified cleaning steps to the PCU module (e.g., programming module 60) to be displayed on a display device of the PCU module.

In some implementations, the processor 202 may transmit the one or more identified cleaning steps to a device (e.g., mobile computing device, mobile phone, and the like) associated with a user (e.g., a biomed technician, a cleaning technician, and the like) assigned with tasks of cleaning the identified medical device to cause the one or more identified cleaning steps to be displayed on a display device associated with device. The processor 202 receives a message indicating completion of cleaning the identified medical device (block 706). This message may be received by way of a user input at the input devices 316 or 320 from the technician performing the cleaning. For example, the technician may input that the cleaning was performed. In some implementations, the message may include sensor data collected by the medical device. For example, a medical device such as a medication preparation workstation may include a camera that can be used to capture images of at least a portion of the workstation during cleaning. The images may be included and, in some instances, analyzed using image recognition or other machine learning algorithms to assess the cleaning.

The processor 202 determines whether the medical device is sufficiently cleaned (block 707). In some implementations, determining cleaning was completed and that the device was sufficiently cleaned are performed simultaneously (e.g., in the same action). For example, when the technician provides input that the cleaning was performed, processor 202 may perform a series of internal checks to confirm, based on the cleaning information received via user input or through its sensors, that all cleaning steps were executed according to a predetermined cleaning procedure. As a further example, processor 202 may confirm that the appropriate cleaning solution identifier was input to the system and cleaning was started within a predetermined appropriate time since the device was flagged for cleaning (e.g., a period of time since infection detection), and that the technician performing the cleaning authenticated to the medical device and is authorized to perform the cleaning for the type of infection and/or authorized to use the type of cleaning solution used on the medical device. In some implementations, after a cleaning step is completed, the processor 202 may receive a message indicating the completion of the cleaning step from the identified medical device 104, and for one or more cleaning steps for which the processor 202 did not receive a message indicating completion, the processor 202 may identify those cleaning steps as incomplete. In some implementations, based on the received message(s), the processor 202 may update a status of the corresponding cleaning step(s) to indicate its completion and may store the updated status in association with the cleaning step(s) in one or more data storage units associated with the device management server 108. The assessment may include analyzing information included in the received messages, such as analysis of images captured during the cleaning process.

In some implementations, the processor 202 may be configured to determine whether the medical device is sufficiently cleaned based on an electronic sensing as to whether each of the functional modules connected to the identified medical device is actually cleaned. The electronic sensing may include detecting one or more signals from a sensor in communication with the processor 202. For example, if the medical device includes a touch-sensitive display screen 314, the cleaning procedure corresponding to the medical device may instruct processor to electronically verify through the touch sensitive display screen that all (or certain) areas of the display screen was actually cleaned. A technician may initiate cleaning by powering on the device and scanning his or her badge. Processor 202 may be programmed to identify that cleaning has been started based on the current location of the device, the technician's login, and/or the input of certain information to the device related to cleaning. When the cleaning process is initiated, the display screen may prompt the technician to clean the display screen, and the medical device may then begin sensing at the screen to verify that each portion of the display screen is touched. In this regard, touching the display screen at all of the predetermined cleaning areas may indicate that the screen was properly cleaned. In some implementations in which the display screen responds an exertion of pressure, processor 202 may require a predetermined threshold amount of pressure and for a predetermined amount of time to be applied at each relevant location of the screen before confirming that the display screen was cleaned.

In some implementations, the processor 202 may cause the display screen to identify each area to be cleaned by way of a graphical indicator on the screen at a specific cleaning location. The graphical indicator may move as each location is determined to have been sufficiently cleaned. The cleaning location and quantity of cleaning needed at a given location may be determined based on the interactions with the medical device. For example, if the medical device maintains a historical record of the clinician interactions that indicate substantial use of buttons or interface elements in the lower-left portion of the medical device, more cleaning may be desirable in the lower-left than for the upper-right. In some implementations, the graphical indicators may identify a swipe or gesture to be performed. For example, it may be desirable to being cleaning using diagonal swipes from corner to corner but then move to spirals or other shapes. In some implementations, the processor 202 may cause the entire screen to change a specific color (e.g., red) and, as the screen senses it is being cleaned (e.g., by way of touch and/or predetermined pressure), the color is changed to a color indicative of having been sufficiently cleaned (e.g., green). In some implementations, the cleaning may be identified as completed when all pixels of the screen are associated with a touch action, or a predetermined amount of pressure being applied during a certain time period after which the technician has initiated cleaning. In some implementations, cleaning is identified as being completed when the entire screen is subject to touch and/or pressure, and the device has identified one or more predetermined swiping actions or movements in conjunction with the applied touch or pressure.

The processor 202 may determine whether a functional module connected to the medical device is cleaned based on a message or signal received from the functional module that indicates that functional module is cleaned. For example, a pump module may include sensors that detect when an a pump component area is accessed and/or when pump components are removed (e.g., to be cleaned). This detection may be collected as cleaning data for analysis (e.g., by processor 202) as to whether the pump module (or medical device) has been sufficiently cleaned. In some implementations, sensors may detect a flow of fluid through components of the medical device and/or functional module and determine whether the medical device and/or functional module was cleaned based on this flow detection. In some implementations, the medical device forwards the received cleaning information to the device management server 108 and, based on the cleaning information, the device management server 108 determines whether the medical device is sufficiently cleaned.

In some implementations, a functional module of the identified medical device may be disconnected from the identified medical device and connected to a second medical, and the device management server 108 may receive information indicating the connection of the functional module to the second medical device. In such implementations, in response to receiving information indicating the connection of the functional module, the processor 202 may determine whether the functional module is cleaned. For example, a memory of the functional module may store a flag indicative of whether the device was cleaned, and processor 202 may read the flag. In some implementations, the memory may store a timestamp associated with the last time the functional module was cleaned, and processor 202 may verify that the timestamp is after a time in which the functional module (or a medical device to which the functional module was previously attached) was identified as requiring cleaning (e.g., infected or exposed to a contaminate). In some implementations, a medical device or functional module may require cleaning periodically, and the timestamp may be indicative of whether a threshold period of time since the medical device or functional module was last cleaned has been exceeded.

If the processor 202 determines that the functional module is not cleaned, then the processor 202 may transmit one or more instructions to the second medical device to disable one or more features of the functional module. In such implementations, if the processor 202 determines that the functional module is cleaned, then the processor 202 updates a status of the functional module to indicate that the functional module is cleaned in the data storage system associated with the device management server 108.

At block 707, if the processor 202 determines that the medical device is not sufficiently cleaned ('NO' at block 707), then the method 700 proceeds to the block 708. The processor 202 may identify one or more incomplete cleaning steps of the cleaning steps associated with the cleaning process (block 708). As described above, in some implementations, for one or more cleaning steps for which the processor 202 did not receive a message indicating completion, the processor 202 may identify those cleaning steps as incomplete. For example, if a cleaning process is associated with three cleaning steps, including a step to clean a large volume pump of/or connected to the identified medical device 104, then a user (e.g., a biomed technician, a cleaning technician, and the like) of the medical device 104 may provide an input to the identified medical device 104 to transmit a message to the device management server 108 indicating that the step of cleaning the large volume pump is completed, and the processor 202 may identify the remaining two steps of the cleaning process as incomplete until the processor 202 receives one or more messages indicating completion of those steps.

In some implementations, the identified medical device 104 may be configured to determine whether a cleaning step is completed and transmit a message to the device management server indicating that the cleaning step is completed. For example, as described above, a medical device 104 may comprise and/or be connected to a display device configured to receive touch inputs and be configured to detect touches at various portions of the display device, and, based on the detected touches at predetermined portion(s) of the display device at a predetermined threshold amount of pressure, the medical device 104 may determine whether the step of cleaning the display device is completed. If the medical device 104 determines that the step of cleaning the display device is completed, then the medical device 104 may automatically transmit a message to the device management server 108 indicating that step of cleaning the display device is completed. The processor 202 identifies the step of cleaning the display device as completed and identifies other cleaning steps, if any, of the cleaning process as incomplete until message(s) indicating completion of the cleaning step(s) are received.

The processor 202 transmits a message indicating the one or more identified incomplete steps to the identified medical device (block 709). In some implementations, the processor 202 may transmit a message and/or indicate in the message that the identified medical device 104 is not sufficiently cleaned. In some implementations, the processor 202 may transmit one or more messages indicating the one or more functional modules of the medical device that are not cleaned. The method 700 proceeds to the block 706.

Returning to block 707, if the processor 202 determines that the medical device is sufficiently cleaned ('YES' at block 707), then the method 700 proceeds to block 710. The processor 202 transmits one or more instructions to the identified medical device to enable (e.g., electronically unlock) the medical device (block 710). The processor 202 may update a state or status of the identified medical device to a status indicating that the medical device is cleaned in a data storage system associated with the device management server 108. In some implementations, the processor 202 updates the status of the one or more functional modules connected to the identified medical device to indicate that the one or more functional modules are cleaned in a data storage system associated with the device management server 108. The processor 202 may additionally or alternatively adjust the medical device to permit further operation. The adjustment may include allowing the handle 52 to operate, retracting an occluder, switching a power circuit on, or the like.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software, or any combination thereof.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method comprising: receiving, by one or more computing devices, an indication that a medical device has been exposed to a predetermined contaminate; providing, to the medical device, responsive to receiving the indication, a first instruction to the medical device, wherein one or more operations of the medical device are disabled responsive to the medical device receiving the first instruction; receiving, by the one or more computing devices, after transmitting the first instruction, cleaning information indicating that a cleaning of the medical device was performed; identifying, by the one or more computing devices, a predetermined cleaning procedure corresponding to the medical device and the contaminate; determining, by the one or more computing devices, based on the cleaning information, that the cleaning of the medical device was performed according to the predetermined cleaning procedure corresponding to the medical device and the contaminate; and providing, by the one or more computing devices, responsive to determining that the medical device was cleaned according to the predetermined cleaning procedure, a second instruction to the medical device, wherein the one or more operations of the medical device are enabled responsive to the medical device receiving the second instruction.

Clause 2. The method of Clause 1, further comprising: receiving user input associated with the medical device, the user input indicating a cleaning solution used to clean the medical device; determining, from the predetermined cleaning procedure, whether the cleaning solution used to clean the medical device is a correct cleaning solution for cleaning the medical device; in response to determining that the cleaning solution is correct, causing one or more cleaning steps to be displayed on a display device associated with the medical device; in response to determining that the cleaning solution is not correct, identifying a correct cleaning solution for the medical device, and transmitting information related to the correct cleaning solution to the medical device.

Clause 3. The method of Clause 2, wherein the cleaning steps include graphically identifying locations on the display screen which require cleaning.

Clause 4. The method of Clause 3, further comprising: sensing, in connection with graphically identifying the locations, whether a touch signal is received at the respective locations; and determining, based on one or more touch signals received on the display screen whether the medical device was cleaned according to the predetermined cleaning procedure.

Clause 5. The method of Clause 1, further comprising: identifying one or more modules connected to the medical device; determining whether the one or more modules are connected to a second medical device; in response to determining that the one or more modules are connected to the second medical device, determining whether the one or more modules were cleaned after being connected to the medical device; and in response to determining that the one or more modules are not cleaned, transmitting an instruction to the second medical device to disable one or more features of the one or more modules.

Clause 6. The method of Clause 5, further comprises: identifying, based on the one or more connected modules, one or more cleaning steps.

Clause 7. The method of Clause 1, further comprising: determining, based on location information of the medical device, whether the medical device is located in a predetermined area of a facility; and in response to determining that the medical device is not located in the predetermined area of the facility, displaying a message to move the medical device to the predetermined area of the facility.

Clause 8. The method of Clause 1, wherein receiving the cleaning information further comprises: receiving, at a server, one or more messages from the medical device regarding steps taken to clean the medical device; and in response to determining that the medical device is cleaned according to the predetermined cleaning procedure, transmitting one or more instructions over a network to enable the medical device.

Clause 9. The method of Clause 8, wherein each of the one or more messages indicates that at least one component of the medical device is cleaned.

Clause 10. The method of Clause 8, further comprising: in response to determining that the medical device is cleaned according to the predetermined cleaning procedure, updating a status of the medical device indicating that the medical device is cleaned in a data storage system.

Clause 11. A system comprising: a memory storing instructions; and one or more processors coupled with the memory and configured to execute the instructions to cause the system to: receive an indication that a medical device has been exposed to a predetermined contaminate; provide, responsive to receiving the indication, a first instruction to the medical device, wherein one or more operations of the medical device are disabled responsive to the medical device receiving the first instruction; receive, after transmitting the instruction, cleaning information indicating that a cleaning of the medical device was performed; identify a predetermined cleaning procedure corresponding to the medical device and the contaminate; determine, based on the cleaning information, that the medical device was cleaned according to the predetermined cleaning procedure corresponding to the medical device and the contaminate; and provide, to the medical device responsive to determining that the cleaning of the medical device was performed according to the predetermined cleaning procedure, a second instruction to the medical device, wherein the one or more operations of the medical device are enabled responsive to the medical device receiving the second instruction.

Clause 12. The system of Clause 11, wherein the one or more processors are configured to execute instructions to cause the system to: receive user input associated with the medical device and indicating a cleaning solution used to clean the medical device; determine, from the predetermined cleaning procedure, whether the cleaning solution used to clean the medical device is a correct cleaning solution for cleaning the medical device; when the cleaning solution is correct, cause one or more cleaning steps to be displayed on a display device associated with the medical device; when the cleaning solution is not correct, identify a correct cleaning solution for the medical device, and transmit information related to the correct cleaning solution to the medical device.

Clause 13. The system of Clause 12, wherein the cleaning steps include graphically identifying locations on the display screen which require cleaning.

Clause 14. The system of Clause 13, wherein the one or more processors are configured to execute instructions to cause the system to: sense, in connection with graphically identifying the locations, whether a touch signal is received at the respective locations; and determine, based on one or more touch signals received on the display screen whether the medical device was cleaned according to the predetermined cleaning procedure.

Clause 15. The system of Clause 11, wherein the one or more processors are configured to execute instructions to cause the system to: identify one or more modules connected to the medical device; determine whether the one or more modules are connected to a second medical device; when the one or more modules are connected to the second medical device, determine whether the one or more modules were cleaned after being connected to the medical device; and when the one or more modules are not cleaned, transmit an instruction to the second medical device to disable one or more features of the one or more modules.

Clause 16. The system of Clause 15, wherein the one or more processors are configured to execute instructions to cause the system to: identify, based on the one or more connected modules, one or more cleaning steps.

Clause 17. The system of Clause 11, wherein the one or more processors are configured to execute instructions to cause the system to: determine, based on location information of the medical device, whether the medical device is located in a predetermined area of a facility; and when the medical device is not located in the predetermined area of the facility, cause a message to move the medical device to the predetermined area of the facility to be displayed on the display device associated with the medical device.

Clause 18. The system of Clause 11, wherein the one or more processors are configured to execute instructions to cause the system to: receive, at a server, one or more messages from the medical device regarding steps taken to clean the medical device; and when the medical device is cleaned according to according to the predetermined cleaning procedure, transmit one or more instructions over a network to enable the medical device.

Clause 19. The system of Clause 18, wherein each of the one or more messages indicate that at least one component of the medical device is cleaned.

Clause 20. The system of Clause 18, wherein the one or more processors are configured to execute instructions to cause the system to: when the medical device is cleaned according to the predetermined cleaning procedure, update a status of the medical device indicating that the medical device is cleaned in a data storage system.

Clause 21. A non-transitory machine-readable medium having instructions stored thereon that, when executed by one or more processors, cause the one or more processors to perform operations comprising: receiving an indication that a medical device has been exposed to a predetermined contaminate; providing, responsive to receiving the indication, a first instruction to the medical device, wherein one or more operations of the medical device are disabled responsive to the medical device receiving the first instruction; receiving, after transmitting the instruction, cleaning information indicating that a cleaning of the medical device was performed; identifying a predetermined cleaning procedure corresponding to the medical device and the contaminate; determining, based on the cleaning information, that the medical device was cleaned according to the predetermined cleaning procedure corresponding to the medical device and the contaminate; and providing, to the medical device responsive to determining that the cleaning of the medical device was performed according to the predetermined cleaning procedure, a second instruction to the medical device, wherein the one or more operations of the medical device are enabled responsive to the medical device receiving the second instruction.

FURTHER CONSIDERATION

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A method comprising:
   determining that a patient or a clinician was exposed to a contaminate based on health information received for the patient or the clinician;
   identifying, by one or more computing devices, a first medical device associated with the patient or the clinician exposed to the contaminate based on a time that the first medical device was used and an identifier for the patient or the clinician being associated with the first medical device;
   providing, to the first medical device by the one or more computing devices, based on determining that the first medical device is associated with the patient or the clinician exposed to the contaminate, a first instruction to electronically lock the first medical device, wherein one or more operations of the first medical device are disabled and cannot be used with a new patient until the first medical device is cleaned after the first medical device is locked;
   receiving, by the one or more computing devices, after locking the first medical device, cleaning information indicating that a cleaning of the first medical device was performed;
   identifying, by the one or more computing devices, based on an identification of the first medical device and the contaminate, a predetermined cleaning procedure corresponding to the first medical device and the contaminate;
   determining, by the one or more computing devices, based on the cleaning information, that the cleaning of the first medical device was performed according to the predetermined cleaning procedure corresponding to the first medical device and the contaminate;
   providing, by the one or more computing devices, based on determining that the first medical device was cleaned according to the predetermined cleaning procedure, a second instruction to the first medical device, wherein the first medical device is unlocked and the one or more operations of the first medical device are enabled responsive to the first medical device receiving the second instruction;
   identifying one or more modules connected to the first medical device when the first medical device is associated with the patient or the clinician;
   determining that the one or more modules are connected to a second medical device;
   after the one or more modules are connected to the second medical device, determining whether the one or more modules were cleaned after being connected to the first medical device; and
   in response to determining that the one or more modules are not cleaned, transmitting an instruction to the second medical device to disable one or more features of the one or more modules.

2. The method of claim 1, further comprising:
   receiving user input associated with the first medical device, the user input indicating a cleaning solution used to clean the first medical device;
   determining, from the predetermined cleaning procedure, whether the cleaning solution used to clean the first medical device is a correct cleaning solution for cleaning the first medical device;
   in response to determining that the cleaning solution is correct, causing one or more cleaning steps to be displayed on a display device associated with the first medical device; and
   in response to determining that the cleaning solution is not correct, identifying a correct cleaning solution for the first medical device, and transmitting information related to the correct cleaning solution to the first medical device.

3. The method of claim 2, wherein the cleaning steps include graphically identifying locations on a display screen of the first medical device which require cleaning.

4. The method of claim 3, further comprising:
   sensing, in connection with graphically identifying the locations, whether a touch signal is received at the respective locations; and
   determining, based on one or more touch signals received on the display screen whether the first medical device was cleaned according to the predetermined cleaning procedure.

5. The method of claim 2, wherein receiving the cleaning information further comprises:
 receiving, at a server, one or more messages from the first medical device regarding steps taken to clean the first medical device; and
 in response to determining that the first medical device is cleaned according to the predetermined cleaning procedure, transmitting one or more instructions over a network to enable the first medical device.

6. The method of claim 5, wherein the one or more messages indicate that at least one component of the first medical device is cleaned, the method further comprising:
 in response to determining that the first medical device is cleaned according to the predetermined cleaning procedure, updating a status of the first medical device indicating that the first medical device is cleaned in a data storage system.

7. The method of claim 1, further comprising:
 identifying, based on the one or more modules, a signal, detectable by the second medical device, indicating completion of one or more cleaning steps,
 wherein determining whether the one or more modules were cleaned is based at least in part on the signal.

8. The method of claim 1, further comprising:
 determining, based on location information of the first medical device, whether the first medical device is located in a predetermined area of a facility; and
 in response to determining that the first medical device is not located in the predetermined area of the facility, displaying a message to move the first medical device to the predetermined area of the facility.

9. A system comprising:
 a memory storing instructions; and
 one or more processors coupled with the memory and configured to execute the instructions to cause the system to:
  determine that a patient or a clinician is exposed to a contaminate based on health information received for the patient or the clinician;
  identify a first medical device associated with the patient or the clinician exposed to the contaminate based on a time that the first medical device was used and an identifier for the patient or the clinician being associated with the first medical device;
  provide, based on determining that the first medical device is associated with the patient or clinician exposed to the contaminate, a first instruction to electronically lock the first medical device, wherein one or more operations of the first medical device are disabled and cannot be used with a new patient until the first medical device is cleaned after the first medical device is locked;
  receive, after locking the first medical device, cleaning information indicating that a cleaning of the first medical device was performed;
  identify, based on an identification of the first medical device and the contaminate, a predetermined cleaning procedure corresponding to the first medical device and the contaminate;
  determine, based on the cleaning information, that the first medical device was cleaned according to the predetermined cleaning procedure corresponding to the first medical device and the contaminate;
  provide, to the first medical device based on determining that the cleaning of the first medical device was performed according to the predetermined cleaning procedure, a second instruction to the first medical device, wherein the first medical device is unlocked and the one or more operations of the first medical device are enabled responsive to the first medical device receiving the second instruction;
  identify one or more modules connected to the first medical device when the first medical device is associated with the patient or the clinician;
  determine that the one or more modules are connected to a second medical device;
  after the one or more modules are connected to the second medical device, determine whether the one or more modules were cleaned after being connected to the first medical device; and
  in response to determining that the one or more modules are not cleaned, transmit an instruction to the second medical device to disable one or more features of the one or more modules.

10. The system of claim 9, wherein the one or more processors are configured to execute instructions to cause the system to:
 receive user input associated with the first medical device and indicating a cleaning solution used to clean the first medical device;
 determine, from the predetermined cleaning procedure, whether the cleaning solution used to clean the first medical device is a correct cleaning solution for cleaning the first medical device;
 when the cleaning solution is correct, cause one or more cleaning steps to be displayed on a display device associated with the first medical device; and
 when the cleaning solution is not correct, identify a correct cleaning solution for the first medical device, and transmit information related to the correct cleaning solution to the first medical device.

11. The system of claim 10, wherein the cleaning steps include graphically identifying locations on a display screen which require cleaning.

12. The system of claim 11, wherein the one or more processors are configured to execute instructions to cause the system to:
 sense, in connection with graphically identifying the locations, whether a touch signal is received at the respective locations; and
 determine, based on one or more touch signals received on the display screen whether the first medical device was cleaned according to the predetermined cleaning procedure.

13. The system of claim 9, wherein the one or more processors are configured to execute instructions to cause the system to:
 determine, after the one or more modules are connected to the second medical device, that the second medical device identified a signal indicating completion of one or more cleaning steps,
 wherein determining whether the one or more modules were cleaned is based at least in part on the signal.

14. The system of claim 9, wherein the one or more processors are configured to execute instructions to cause the system to:
 determine, based on location information of the first medical device, whether the first medical device is located in a predetermined area of a facility; and
 when the first medical device is not located in the predetermined area of the facility, cause a message to move the first medical device to the predetermined area of the facility to be displayed on a display device associated with the first medical device.

15. The system of claim 9, wherein the one or more processors are configured to execute instructions to cause the system to:
 receive, at a server, one or more messages from the first medical device regarding steps taken to clean the first medical device; and
 when the first medical device is cleaned according to according to the predetermined cleaning procedure, transmit one or more instructions over a network to enable the first medical device.

16. The system of claim 15, wherein the one or more messages indicate that at least one component of the first medical device is cleaned.

17. The system of claim 15, wherein the one or more processors are configured to execute instructions to cause the system to:
 when the first medical device is cleaned according to the predetermined cleaning procedure, update a status of the first medical device indicating that the first medical device is cleaned in a data storage system.

18. A non-transitory machine-readable medium having instructions stored thereon that, when executed by one or more processors, cause the one or more processors to perform operations comprising:
 determining that a patient or a clinician was exposed to a contaminate based on health information received for the patient or the clinician;
 identifying a first medical device associated with the patient or the clinician exposed to the contaminate based on a time that the first medical device was used and an identifier for the patient or the clinician being associated with the first medical device;
 providing, based on determining that the first medical device is associated with the patient or the clinician exposed to the contaminate, a first instruction to electronically lock the first medical device, wherein one or more operations of the first medical device are disabled and cannot be used with a new patient until the first medical device is cleaned after the first medical device is locked;
 receiving, after locking the first medical device, cleaning information indicating that a cleaning of the first medical device was performed;
 identifying, based on an identification of the first medical device and the contaminate, a predetermined cleaning procedure corresponding to the first medical device and the contaminate;
 determining, based on the cleaning information, that the first medical device was cleaned according to the predetermined cleaning procedure corresponding to the first medical device and the contaminate; and
 providing, to the first medical device based on determining that the cleaning of the first medical device was performed according to the predetermined cleaning procedure, a second instruction to the first medical device, wherein the first medical device is unlocked and the one or more operations of the first medical device are enabled responsive to the first medical device receiving the second instruction;
 identifying one or more modules connected to the first medical device when the first medical device is associated with the patient or the clinician;
 determining that the one or more modules are connected to a second medical device;
 after the one or more modules are connected to the second medical device, determining whether the one or more modules were cleaned after being connected to the first medical device; and
 in response to determining that the one or more modules are not cleaned, transmitting an instruction to the second medical device to disable one or more features of the one or more module.

* * * * *